United States Patent [19]

Patel

[11] 4,338,257

[45] Jul. 6, 1982

[54] BENZOYL ARYLTHIOUREAS AND USE AS PLANT GROWTH REGULATORS

[75] Inventor: Natu R. Patel, Overland Park, Kans.

[73] Assignee: Gulf Oil Corporation, Pittsburgh, Pa.

[21] Appl. No.: 238,338

[22] Filed: Feb. 26, 1981

Related U.S. Application Data

[62] Division of Ser. No. 121,542, Mar. 4, 1980, abandoned.

[51] Int. Cl.³ .................. C07C 161/02; C07C 161/04; C07C 149/40
[52] U.S. Cl. ................................... 260/454; 562/439; 562/432; 560/18
[58] Field of Search .......................... 260/454; 560/18; 562/439, 432

[56] References Cited

U.S. PATENT DOCUMENTS 2,686,806  8/1954  Huebner et al. ..................... 260/454

Primary Examiner—John M. Ford
Assistant Examiner—Robert C. Whittenbaugh
Attorney, Agent, or Firm—Deane E. Keith; Forrest D. Stine; Carl A. Cline

[57] ABSTRACT

Novel compounds having the structural formula

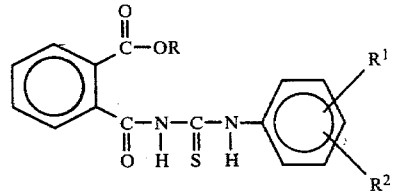

in which R is H or agriculturally acceptable salts thereof, or $C_1$ to $C_4$ alkyl and $R^1$ and $R^2$ are hydrogen or $C_1$ to $C_4$ alkyl, alkoxy or carbalkoxy, halogen, thiocyano, hydroxy, phenoxy, methylenedioxy or methylthio are useful as plant growth regulators, particularly to increase fruit set with minimum deformative side effects.

38 Claims, No Drawings

BENZOYL ARYLTHIOUREAS AND USE AS PLANT GROWTH REGULATORS

This is a division of application Ser. No. 121,542, filed Mar. 4, 1980, now abandoned.

DESCRIPTION OF THE INVENTION

Plant growth regulators may be used for many desirable purposes, as for example, to increase fruit set, limit the height of plants, increase flowering, reduce axillary growth or "suckering". In many instances, however, the desirable effects of growth regulators are accompanied by side effects that are so severe that the compounds are only useful in practice as selective herbicides.

I have discovered a class of compounds which are useful as growth regulators but which in general, do not produce severe side effects. These compounds produce effects which are relatively free from epinasty, are fairly mild with respect to formative effects and are seldom severely phytotoxic. In instances in which phytotoxic effects are observed, they are selectively apparent in a very small number of species.

Briefly, these novel growth regulators are benzoyl arylthiourea compounds having the structural formula:

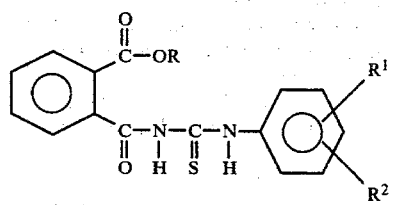

in which R is H or an agriculturally acceptable salt thereof, or $C_1$ to $C_4$ alkyl and $R^1$ and $R^2$ are hydrogen or $C_1$ to $C_4$ alkyl, alkoxy or carbalkoxy, halogen, thiocyano, hydroxy, phenoxy, methylenedioxy, or methylthio.

SYNTHESIS OF THE GROWTH REGULANTS

The novel compounds are conveniently synthesized from commercially available materials by a sequence of reactions which may be carried out in a single reactor according to the following scheme:

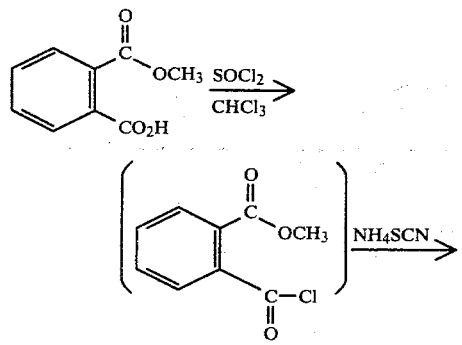

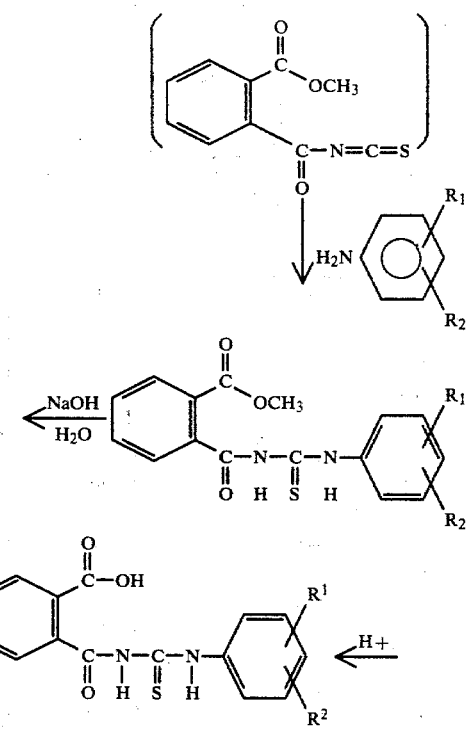

The following procedure is illustrative of the method:

1-(2-CARBOMETHOXYBENZOYL)-3-(2-METHYLPHENYL) THIOUREA

To a 25 ml of dry chloroform, 5.4 g (0.03 m) methyl hydrogen phthalate and 3.9 g (0.033 m) thionyl chloride is added. Stir and reflux for 3 hours and cool to room temperature. To this solution 2.3 g (0.03 m) ammonium thiocyanate is added and the mixture is stirred for 3 hours at room temperature until it changed to bellow. Finally, 3.2 g (0.03 m) 2-methylaniline is added and stirred at room temperature overnight. The mixture is added to water and then some hexane is added to give fine precipitates. Filter, wash with water, hexane and dry to give 6.1 g, desired product, m.p. 143-45, yield 62%.

Compounds listed in the following table have been made by the illustrated method and have been characterized by means of infrared and nuclear magnetic resonance spectra. Melting points are uncorrected.

Compounds of the formula

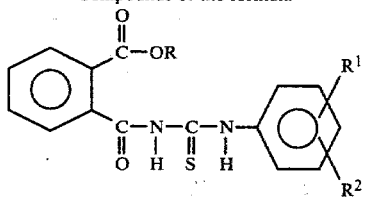

| Compound No. | $R^1$ | $R^2$ | mp (°C.) |
|---|---|---|---|
| in which R is methyl | | | |
| 2497 | H | H | 147–154 |
| 2498 | 4-methyl | H | 174–180 |
| 2655 | 2-methyl | H | 143–145 |
| 2656 | 3-methyl | H | 125–129 |
| 2657 | 4-fluoro | H | 150–154 |

-continued

Compounds of the formula

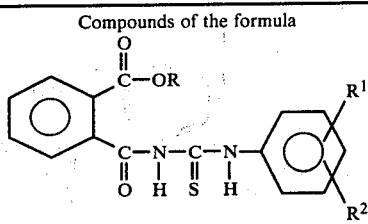

| Compound No. | R¹ | R² | mp (°C.) |
|---|---|---|---|
| 2660 | 2-methyl | 3-methyl | 172–173 |
| 2664 | 2-carbomethoxy | H | 160–161 |
| 2667 | 4-carboethoxy | H | 159–162 |
| 2988 | 2-methyl | 6-methyl | 210–211 |
| 2989 | 2-chloro | H | 160–162 |
| 2990 | 2-fluoro | H | 160–162 |
| 3258 | 2-methoxy | H | 151–154 |
| 3259 | 2-methylthio | H | 177–179 |
| 3260 | 2-bromo | H | 171–173 |
| 3261 | 2-methyl | 4-chloro | 163–166 |
| 3262 | 2-methyl | 4-methyl | 161–163 |
| 3263 | 2-chloro | 4-methyl | 198–199 |
| 3264 | 2-methyl | 4-fluoro | 165–167 |
| 3265 | 2-fluoro | 4-fluoro | 169–172 |
| 3266 | 2-methyl | 3-chloro | 195–200 |
| 3381 | 2-ethyl | H | 140–142 |
| 4311 | 2-chloro | 4-chloro | dec 185 |
| 4312 | 2-methyl | 4-thiocyano | 169–174 |
| 4438 | 3-methoxy | H | 157–160 |
| 4439 | 4-methoxy | H | 154–157 |
| 4515 | 2-methoxy | 5-methoxy | 184–187 |
| 4516 | 3-methoxy | 5-methoxy | 178–180 |
| 4580 | 3-hydroxy | H | 166–172 |
| 4581 | 3-phenoxy | H | syrup |
| 4584 | 4-hydroxy | H | 178–182 |
| 4590 | 2-hydroxy | H | 195–197 |
| 4622 | 4-ethoxy | H | 148–151 |
| 4623 | 3,4-methylenedioxy | | 191–193 |
| Compounds in which R is H | | | |
| 3742 | 2-methyl | H | 171–174 |
| 3773 | 2-methyl | 4-chloro | 172–175 |
| 3774 | 2-methyl | 4-methyl | 170–172 |
| 3778 | 2-methyl | 4-fluoro | 175–176 |

USE OF THE GROWTH REGULATORS

By application of an effective amount of the growth regulators, either pre- or post-emergently, various effects on young plants become apparent. These effects may be demonstrated by means of the following illustrative procedures.

PRE-EMERGENT APPLICATION

Disposable paper trays about 2½ inches deep which were filled with soil were sprayed with aqueous spray mixtures at a rate of 5 lb. of active chemical per acre of sprayed area, then were seeded with 6 species of plant seeds and were covered with about ¼ inch of soil. The spray mixtures were prepared by dissolving the proper amount of growth regulant compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule.

| DEGREE OF EFFECT |
|---|
| 0 = no effect |
| 1 = slight effect, plants recovered |
| 2 = moderate effect, injury to 26 to 75 percent |
| 3 = severe effect, injury to 76 to 99 percent of foliage |
| 4 = maximum effect (all plants died) |

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal. per acre with a spray mixture containing no growth regulator. Plant injury was again rated according to the schedule disclosed above.

Observations of growth regulator effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |
| Chlorosis | C |

In the table below there are tabulated various observations of pre- and post-emergent herbicidal and growth regulator effects of the compounds disclosed above.

EFFECT OF COMPOUNDS ON PLANT LIFE

| | Pre-emergent Effects | | | | | Post-emergent Effects | | | | | | |
|---|---|---|---|---|---|---|---|---|---|---|---|---|
| Compound No. | Digitaria sanguinalis | Celosia plymosa | Bromus inermis | Setaria italica | Raphanus sativus | Beta vulgaris | Setaria italica | Medicago sativa | Avena sativa | Raphanus sativus | Beta vulgaris | Lycopersicum esculentum | Comments |
| 2497 | 0 | 0 | 0 | 0 | 0 | 0 | N3 | F2G2 | N1 | G2N2 | G1 | 0 | |
| 2498 | 0 | 0 | 0 | 0 | 0 | 0 | N1 | F1 | 0 | 0 | F2 | 0 | |
| 2655 | G1 | 0 | 0 | 0 | 0 | 0 | F1G1 | F1 | 0 | N1 | F1 | F2G2 | |
| 2656 | 0 | 0 | 0 | 0 | 0 | 0 | G2N2 | G3N3 | G1N1 | G1N2 | G1 | N1 | |
| 2657 | 0 | 0 | 0 | 0 | 0 | 0 | N1 | G2N2 | 0 | G2N2 | G1 | F1 | |
| 2660 | 0 | 0 | 0 | 0 | 0 | 0 | 0 | N1 | 0 | 0 | 0 | 0 | |
| 2664 | 0 | 0 | 0 | 0 | 0 | 0 | 0 | F1 | 0 | F1 | F2 | F1 | |
| 2667 | 0 | 0 | 0 | 0 | 0 | 0 | 0 | 0 | 0 | 0 | 0 | F1 | |
| 2988 | 0 | 0 | 0 | 0 | 0 | 0 | 0 | 0 | 0 | 0 | F1 | 0 | |

EFFECT OF COMPOUNDS ON PLANT LIFE

| Compound No. | Pre-emergent Effects | | | | | | Post-emergent Effects | | | | | | Comments |
|---|---|---|---|---|---|---|---|---|---|---|---|---|---|
| | Digitaria sanguinalis | Celosia plymosa | Bromus inermis | Setaria italica | Raphanus sativus | Beta vulgaris | Setaria italica | Medicago sativa | Avena sativa | Raphanus sativus | Beta vulgaris | Lycopersicum esculentum | |
| 2989 | 0 | 0 | 0 | 0 | 0 | 0 | F1 | 0 | 0 | 0 | F2G2 | F2G2 | |
| 2990 | 0 | 0 | 0 | 0 0 | 0 | 0 | G1N2 | 0 | 0 | N1 | F2 0 | F1 fruit set | Increased |
| 3258 | 0 | — | F1 | 0 | 0 | 0 | N1 | F2G2 | F1 | F1 | F2G2 | N1 | |
| 3259 | 0 | 0 | F2 | 0 | 0 | 0 | 0 | 0 | F1 | 0 | F1 | F1 | |
| 3260 | 0 | 0 | 0 | 0 | 0 | 0 | 0 | F1 | F1 | 0 | F2G2 | 0 | |
| 3261 | 0 | 0 | 0 | 0 | 0 | 0 | 0 | F2 | 0 | 0 | F1 | F1 | |
| 3262 | 0 | 0 | 0 | 0 | 0 | 0 | 0 | F1 | 0 | 0 | F1 | F1 | Shape of fruit is changed |
| 3263 | 0 | 0 | 0 | 0 | 0 | 0 | 0 | 0 | 0 | 0 | 0 | 0 | |
| 3264 | 0 | 0 | 0 | 0 | 0 | 0 | 0 | N2F1 | 0 | F1 | N4 | 0 | |
| 3265 | 0 | 0 | 0 | 0 | 0 | 0 | 0 | F1 | F1 | F1N1 | F2G2 | F1 | Increased fruit set |
| 3266 | 0 | 0 | 0 | 0 | 0 | 0 | 0 | 0 | 0 | 0 | F3 | 0 | |
| 3381 | 0 | 0 | F1 | 0 | 0 | F1 | 0 | 0 | 0 | F1 | F1 | 0 | |
| 4311 | 0 | 0 | 0 | 0 | 0 | 0 | 0 | F1 | 0 | F1 | 0 | 0 | |
| 4312 | 0 | 0 | 0 | 0 | 0 | 0 | 0 | F1 | 0 | F1 | 0 | 0 | |
| 3742 | 0 | 0 | 0 | 0 | 0 | 0 | | | | | | | |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor El-719), 20 wt. percent xylene and 20 wt. percent deodorized kerosene, then bringing total volume up to 80 ml by addition of a 0.156 wt. percent aqueous solution of liquid nonionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of the arithmetic mean of the numbers on untreated plants was observed within approximately three weeks after spray treatment and the results are tabulated below. The severity of growth regulatory effect on the plants was estimated on a scale of 0 to 10 and is also recorded in the following table:

GROWTH REGULATING EFFECTS ON TWO SPECIES

| | | Soja max | | Lycopersicum esculentum | |
|---|---|---|---|---|---|
| Comp'd. No. | Rate oz/A | Pod Count[1] Percent in Comparison to Untreated Plants | Severity of Growth Regulating Effect[2] | Fruit Count[1] Percent in Comparison to Untreated Plants | Severity of Growth Regulating Effect[2] |
| 2655 | 16 | 84 | 0.5 | 111 | 0.5 |
| | 4 | 75 | 0 | 104 | 0 |
| | 1 | 84 | 0 | 107 | 0 |
| 2656 | 16 | 27 | 0 | 126 | 1.5 |
| | 4 | 164 | 0 | 104 | 0 |
| | 1 | 136 | 0 | 93 | 0 |
| 2989 | 16 | 106 | 2 | 100 | 1.5 |
| | 4 | 176 | 0 | 117 | 0.5 |
| | 1 | 141 | 0 | 117 | 0 |
| 2990 | 16 | 318 | 3 | 125 | 2.5 |
| | 4 | 212 | 1 | 133 | 0.5 |
| | 1 | 176 | 0 | 125 | 0 |
| 3258 | 16 | 71 | 1 | 100 | 1 |
| | 4 | 106 | 0 | 121 | 0 |
| | 1 | 176 | 0 | 142 | 0 |
| 3260 | 16 | 106 | 0 | 117 | 0.5 |
| | 4 | 141 | 0 | 121 | 0 |
| | 1 | 71 | 0 | 108 | 0 |
| 3261 | 16 | 141 | 0 | 142 | 1 |
| | 4 | 141 | 0 | 125 | 0 |
| | 1 | 35 | 0 | 125 | 0 |
| 3742 | 16 | 450 | 2.5 | 112 | 1 |
| | 4 | 75 | 1 | 104 | 0 |
| | 1 | 150 | 93 | 0 | |
| 3259 | 16 | 200 | 0 | 90 | 0 |
| | 4 | 0 | 0 | 105 | 0 |
| | 1 | 50 | 0 | 108 | 0 |
| 3262 | 16 | 100 | 0 | 112 | 0 |
| | 4 | 50 | 0 | 101 | 0 |
| | 1 | 0 | 0 | 87 | 0 |
| 3264 | 16 | 700 | 0 | 90 | 0.5 |
| | 4 | 150 | 0 | 108 | 0 |
| | 1 | 0 | 0 | 105 | 0 |
| 3265 | 16 | 300 | 0 | 134 | 0 |
| | 4 | 0 | 0 | 141 | 0 |
| | 1 | 50 | 0 | 112 | 0 |
| 3266 | 16 | 0 | 0 | 108 | 0 |
| | 4 | 50 | 0 | 112 | 0 |

|  | Soja max | | | Lycopersicum esculentum | |
|---|---|---|---|---|---|
| Comp'd. No. | Rate oz/A | Pod Count[1] Percent in Comparison to Untreated Plants | Severity of Growth Regulating Effect[2] | Fruit Count[1] Percent in Comparison to Untreated Plants | Severity of Growth Regulating Effect[2] |
| 1 | | 0 | 0 | 90 | 0 |

[1] Check = 100
[2] Greenhouse rating on scale of 0, no effect; 10, total kill.

The information presented in tabular form herein will enable a worker in the art to make a selection from among the growth regulator compounds of the invention and to make some judgment with regard to application rates, depending upon the effect which is desired.

The growth regulator compounds are usually employed in compositions containing from 0.1 to 95 weight percent active ingredient in combination with a surface active agent and inert carriers or diluents, as in emulsifiable compositions, granules and dust formulations, in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The ester type growth regulators may be easily converted to salts of the isothioureido type or may be hydrolyzed in aqueous alkali to yield carboxylic acid salts. It will be understood that it may be more convenient to formulate and apply the agriculturally acceptable salts of the growth regulators. Various ammonium and amine salts are convenient to prepare and use and are desirable for agricultural use because they are eventually decomposed and leave no permanent residues. It is well understood in the art that salts which leave heavy metals or other toxic residues are not agriculturally acceptable.

I claim:
1. The compound having the structural formula:

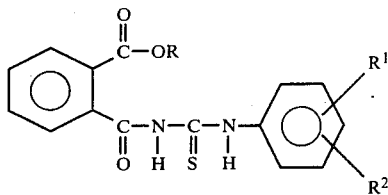

in which R is H or an agriculturally acceptable salt thereof, or $C_1$ to $C_4$ alkyl and $R^1$ and $R^2$ are hydrogen or $C_1$ to $C_4$ alkyl, alkoxy or carbalkoxy, halogen, thiocyano, hydroxy, phenoxy, or methylthio.

2. The compound of claim 1 in which R is methyl and $R^1$ and $R^2$ are both H.

3. The compound of claim 1 in which R is methyl, $R^1$ is 4-methyl and $R^2$ is H.

4. The compound of claim 1 in which R is methyl, $R^1$ is 2-methyl and $R^2$ is H.

5. The compound of claim 1 in which R is methyl, $R^1$ is 3-methyl and $R^2$ is H.

6. The compound of claim 1 in which R is methyl, $R^1$ is 4-fluoro and $R^2$ is H.

7. The compound of claim 1 in which R is methyl, $R^1$ is 2-methyl and $R^2$ is 3-methyl.

8. The compound of claim 1 in which R is methyl, $R^1$ is 2-carbomethoxy and $R^2$ is H.

9. The compound of claim 1 in which R is methyl, $R^1$ is 4-carboethoxy and $R^2$ is H.

10. The compound of claim 1 in which R is methyl, $R^1$ is 2-methyl and $R^2$ is 6-methyl.

11. The compound of claim 1 in which R is methyl, $R^1$ is 2-chloro and $R^2$ is H.

12. The compound of claim 1 in which R is methyl, $R^1$ is 2-fluoro and $R^2$ is H.

13. The compound of claim 1 in which R is methyl, $R^1$ is 2-methoxy and $R^2$ is H.

14. The compound of claim 1 in which R is methyl, $R^1$ is 2-methylthio and $R^2$ is H.

15. The compound of claim 1 in which R is methyl, $R^1$ is 2-bromo and $R^2$ is H.

16. The compound of claim 1 in which R is methyl, $R^1$ is 2-methyl and $R^2$ is 4-chloro.

17. The compound of claim 1 in which R is methyl, $R^1$ is 2-methyl and $R^2$ is 4-methyl.

18. The compound of claim 1 in which R is methyl, $R^1$ is 2-chloro and $R^2$ is 4-methyl.

19. The compound of claim 1 in which R is methyl, $R^1$ is 2-methyl and $R^2$ is 4-fluoro.

20. The compound of claim 1 in which R is methyl, $R^1$ is 2-fluoro and $R^2$ is 4-fluoro.

21. The compound of claim 1 in which R is methyl, $R^1$ is 2-methyl and $R^2$ is 3-chloro.

22. The compound of claim 1 in which R is methyl, $R^1$ is 2-ethyl and $R^2$ is H.

23. The compound of claim 1 in which R is methyl, $R^1$ is 2-chloro and $R^2$ is 4-chloro.

24. The compound of claim 1 in which R is methyl, $R^1$ is 2-methyl and $R^2$ is 4-thiocyano.

25. The compound of claim 1 in which R is methyl, $R^1$ is 3-methoxy and $R^2$ is H.

26. The compound of claim 1 in which R is methyl, $R^1$ is 3-methoxy and $R^2$ is H.

27. The compound of claim 1 in which R is methyl, $R^1$ is 4-methoxy and $R^2$ is H.

28. The compound of claim 1 in which R is methyl, $R^1$ is 2-methoxy and $R^2$ is 5-methoxy.

29. The compound of claim 1 in which R is methyl, $R^1$ is 3-methoxy and $R^2$ is 5-methoxy.

30. The compound of claim 1 in which R is methyl, $R^1$ is 3-hydroxy and $R^2$ is H.

31. The compound of claim 1 in which R is methyl, $R^1$ is 3-phenoxy and $R^2$ is H.

32. The compound of claim 1 in which R is methyl, $R^1$ is 4-hydroxy and $R^2$ is H.

33. The compound of claim 1 in which R is methyl, $R^1$ is 2-hydroxy and $R^2$ is H.

34. The compound of claim 1 in which R is methyl, $R^1$ is 4-ethoxy and $R^2$ is H.

35. The compound of claim 1 in which R is H, $R^1$ is 2-methyl and $R^2$ is 4-chloro.

36. The compound of claim 1 in which R is H, $R^1$ is 2-methyl and $R^2$ is 4-methyl.

37. The compound of claim 1 in which R is H, $R^1$ is 2-methyl and $R^2$ is 4-fluoro.

38. The compound of claim 1 in which R is H, $R^1$ is 2-methyl and $R^2$ is H.

* * * * *